United States Patent [19]

Ziggiotti et al.

[11] Patent Number: 4,970,236

[45] Date of Patent: Nov. 13, 1990

[54] MOUTH-SOLUBLE PHARMACEUTICAL COMPOSITIONS CONTAINING ACETYL-CYSTEINE

[75] Inventors: Antonio Ziggiotti, Vezia, Switzerland; Paolo Lualdi, Grandate, Italy

[73] Assignee: Altergon S.A., Lugano, Switzerland

[21] Appl. No.: 343,350

[22] Filed: Apr. 26, 1989

[30] Foreign Application Priority Data

Apr. 29, 1988 [IT]  Italy .................... 20386 A/88

[51] Int. Cl.$^5$ .................... A61K 7/22; A61K 31/195
[52] U.S. Cl. .................... 514/562; 424/54; 424/440; 424/441
[58] Field of Search .................... 424/54, 440, 441; 514/562

[56] References Cited

U.S. PATENT DOCUMENTS

| | | | |
|---|---|---|---|
| Re. 29,256 | 6/1977 | Joullie et al. | 514/562 |
| 2,888,380 | 5/1959 | Brown et al. | 514/562 |
| 3,091,569 | 5/1963 | Sheffner | 514/562 |
| 4,305,958 | 12/1981 | Fujita et al. | 514/562 |
| 4,559,360 | 12/1985 | Puricelli | 514/562 |
| 4,724,239 | 2/1988 | Morgan | 514/563 |
| 4,767,785 | 8/1988 | Georgieff | 514/562 |
| 4,794,124 | 12/1988 | Yamamoto et al. | 514/562 |
| 4,829,087 | 5/1989 | Ammon | 514/562 |

FOREIGN PATENT DOCUMENTS

| | | |
|---|---|---|
| 3723734 | 2/1988 | Fed. Rep. of Germany . |
| 3723735 | 2/1988 | Fed. Rep. of Germany . |
| 3667M | 11/1965 | France .................... 514/562 |
| 2192789 | 1/1988 | United Kingdom . |
| 2192790 | 1/1988 | United Kingdom . |

OTHER PUBLICATIONS

Nara et al. C.A.85:83172m (1976)(Cysteine Derivs. & Sugars: Fructose, Glucose, Cactose).

Gazzinaga et al., C.A.108: 226872w (1988) of Ger. Offen DE 372373y, Feb. 4, 1988.

Gazzinaga et al., C.A.108: 226873x (1988) of Ger. Offen DE 3723735, Feb. 4, 1988.

*Primary Examiner*—Shep K. Rose
*Attorney, Agent, or Firm*—Birch, Stewart, Kolasch & Birch

[57] ABSTRACT

A month-soluble pharmaceutical composition comprising acetylcysteine, alkaline, bicarbonates, carbohydrates and fruit flavoring, produced in the form of tablets for treating affections of the oral cavity.

4 Claims, No Drawings

MOUTH-SOLUBLE PHARMACEUTICAL COMPOSITIONS CONTAINING ACETYL-CYSTEINE

FIELD OF THE INVENTION

This invention relates to mouth-soluble pharmaceutical compositions containing acetylcysteine for treating affections of the oral cavity.

KNOWN ART

It is known to use acetylcysteine as a mucolytic and expectorant for the purpose of fluidizing the dense viscous secretions of the respiratory system in bronchitis, bronchial catarrh, emphysema, mucoviscidosis, etc.

Known compositions are available for systemic treatment of respiratory diseases or for aerosol treatment.

They are prepared in granular or tablet form to be dissolved in water and immediately swallowed, in capsule form for oral use, or in aerosol vials.

Compositions containing acetylcysteine for dissolving in the mouth are not known, although such compositions would be of use in treating affections of the oral cavity.

This limitation is due to the fact that acetylcysteine is a substance with high acidity (pKa=3.24) and its continued presence in the mouth causes severe aggression of the mucous membrane of the tongue and oral cavity. In addition, acetylcysteine has an extremely unpleasant taste and this characteristic is a further contraindication with regard to its dissolving in the mouth.

SUMMARY OF THE INVENTION

The aim of the present invention is to provide pharmaceutical compositions containing acetylcysteine for dissolving in the mouth, which obviate the drawbacks known in the art and in, particular, the mucous membrane aggression and unpleasant taste.

Said compositions are characterised by comprising acetylcysteine, alkaline bicarbonates, carbohydrates and fruit flavouring.

DETAILED DESCRIPTION OF THE INVENTION

The characteristics and advantages of the pharmaceutical compositions according to the invention will be apparent from the detailed description given hereinafter by way of non-limiting examples.

Said pharmaceutical compositions comprise acetylcysteine, alkaline bicarbonates, suitably chosen carbohydrates and small quantities of fruit flavouring.

The alkaline bicarbonates used are sodium bicarbonate and potassium bicarbonate in a NaHCO$_3$/KHCO$_3$ weight ratio of between 93:7 and 97:3. The weight ratio of the bicarbonate mixture to the acetylcysteine is between 45:100 and 55:100.

Neither saccharose nor glucose can be chosen as carbohydrates because of their diabetogenic and cariogenic nature, in consideration of the long period for which they remain in the mouth.

In addition, experimental tests carried out on compositions containing lysine or arginine or arginine/sorbitol or lysine/sorbitol or citrates have not satisfactorily solved the problem of poor taste.

However a satisfactory solution to the taste problem has been surprisingly found by using sorbitol/fructose, sorbitol/xylitol and xylitol/fructose with the two carbohydrates in a weight ratio of between 0.8:1.2 and 1.2:0.8. The weight ratio of carbohydrates to the acetylcysteine is between 20:1 and 50:1.

The flavouring is preferably chosen from orange, lemon, grapefruit, peach and apricot. They are contained in a small quantity in the compositions.

The compositions of the invention are produced preferably in the form of tablets with an acetylcysteine content of between 50 and 300 mg per dose.

Said compositions are suitable to be dissolved in the mouth. They are not aggressive in any way to the mucous membrane and have a pleasant taste.

This form of administration allows the acetylcysteine to be distributed at the oropharyngeal level followed by ingestion and gastric absorption.

In this manner the compositions according to the invention find useful application in oral cavity affections of inflammatory origin such as glossitis, gingivitis, stomatitis, leukoplakia, etc., in affections caused by abnormal secretion of mucus, such as mucocele, oral manifestations of the Siogren syndrome etc., and in halitosis.

Finally, said compositions produce the pleasant effect of freshness which is particularly desirable in the case of inflamed mucous membranes. In addition, the presence of small quantities of fruit flavouring further improves their taste.

We claim:

1. A mouth-soluble pharmaceutical tablet composition which is dissolvable in the oral cavity, comprising:
   acetylcysteine;
   a mixture of sodium bicarbonate and potassium bicarbonate wherein the weight ratio NaHCO$_3$/KHCO$_3$ is between 93:7 and 97:3, and wherein said mixture is present in an amount of 45–55 parts by weight based on 100 parts by weight of acetylcysteine;
   a mixture of two carbohydrates selected from the group consisting of sorbitol, xylitol and fructose, wherein the weight ratio between said two carbohydrates is from about 0.8 to 1.2 and 1.2 to 0.8, and wherein said carbohydrate mixture is present in an amount of 20–50 parts by weight based on 1 part by weight of acetylcysteine; and
   a fruit flavoring.

2. The composition according to claim 1 wherein said first flavoring is chosen from orange, lemon, grapefruit, peach and apricot flavoring.

3. The composition according to claim 1 having an acetylcysteine content of between 50 and 300 mg per dose.

4. A method for treating affections of the oral cavity which comprises administering to a host in need thereof the pharmaceutical tablet composition according to claim 1.

* * * * *